United States Patent [19]

Baron et al.

[11] Patent Number: 5,707,973
[45] Date of Patent: Jan. 13, 1998

[54] SULFATED POLYSACCHARIDS FOR TREATMENT OR PREVENTION OF THROMBOSES

[75] Inventors: Jean-Pierre Baron, Combs La Ville; André Brun, Maisons Alfort; Hendrik Hemker, Maastricht; André Uzan, Paris, all of France

[73] Assignee: Rhone-Poulenc Rorer S.A., Antonv, France

[21] Appl. No.: 353,161

[22] Filed: Dec. 9, 1994

Related U.S. Application Data

[63] Continuation of Ser. No. 137,137, filed as PCT/FR92/00352, Apr. 21, 1992 published as WO92/18544, Oct. 29, 1992, abandoned.

[30] Foreign Application Priority Data

Apr. 23, 1991 [FR] France .................. 91 04991

[51] Int. Cl.$^6$ .............. A61K 31/725; C08B 37/10
[52] U.S. Cl. .................................. 514/56; 536/21
[58] Field of Search ..................... 536/21; 514/56

[56] References Cited

U.S. PATENT DOCUMENTS

| | | | |
|---|---|---|---|
| 4,386,025 | 5/1983 | Jordan | 530/393 |
| 4,401,662 | 8/1983 | Lormeau et al. | 424/183 |
| 4,446,126 | 5/1984 | Jordan | 424/183 |
| 4,446,314 | 5/1984 | Jordan | 536/21 |
| 4,450,104 | 5/1984 | Jordan | 530/396 |
| 4,818,816 | 4/1989 | Petitou et al. | 536/55.2 |
| 4,826,827 | 5/1989 | Lormeau et al. | 514/56 |
| 4,841,041 | 6/1989 | Boeckel et al. | 536/118 |
| 5,032,679 | 7/1991 | Brandley et al. | 536/21 |
| 5,084,564 | 1/1992 | Vila et al. | 514/56 |
| 5,389,618 | 2/1995 | Debrie | 514/56 |

FOREIGN PATENT DOCUMENTS

| | | |
|---|---|---|
| 0 027 089 | 10/1980 | European Pat. Off. . |
| 0 037 319 | 3/1981 | European Pat. Off. . |
| 0 040 144 | 5/1981 | European Pat. Off. . |
| 0 064 452 | 4/1982 | European Pat. Off. . |
| 0 084 999 | 1/1983 | European Pat. Off. . |
| 0244235 | 4/1987 | European Pat. Off. . |
| 0 301 618 | 7/1988 | European Pat. Off. . |
| 0337327 | 10/1989 | European Pat. Off. . |
| 2548672 | 1/1985 | France . |
| 2 622 450 | 11/1987 | France . |
| 2 663 639 | 6/1990 | France . |
| 29 45 595 A1 | 11/1979 | Germany . |
| 3608685 | 9/1987 | Germany . |
| WO 90/04607 | 10/1989 | WIPO . |

OTHER PUBLICATIONS

Thrombosis Res., 38, 389–399 (1985), Mestre et al. Comparative Effects of Heparin and Pk 10169, A Low Molecular Weight Fraction, in a Canine Model of Arterial Thombosis, Month not available.

Thromb. Haemostasis, 63(3), 488–492 (1990), Kovensky et al., Low Anticoagulant Activity of High Sulphated Heparan Sulphates, month not available.

Primary Examiner—Kathleen K. Fonda
Attorney, Agent, or Firm—Michael B. Martin; Raymond S. Parker, III; Paul R. Darkes

[57] ABSTRACT

The invention relates to new mixtures of sulfated oligosaccharides having the general structure of heparin constitutive oligosaccharides, having an average molecular mass of 6±0.6 kD, a polydispersiveness close to 1 and the capacity of inhibiting the production of thrombin. The invention also relates to their preparation and to pharmaceutical compositions containing them.

12 Claims, No Drawings

SULFATED POLYSACCHARIDS FOR TREATMENT OR PREVENTION OF THROMBOSES

This is a continuation of application Ser. No. 08/137,137 filed on Oct. 21, 1993, now abandoned, which is the U.S. national stage entry under 35 U.S.C. § 371 of PCT/FR92/00352, filed on Apr. 21, 1992 published as WO92/18544, Oct. 29, 1992.

The present invention relates to the field of low-molecular weight polysaccharides. More specifically, it relates to oligosaccharide compositions possessing excellent pharmacological and antithrombotic properties.

Generally, antithrombotic treatments require the use of two main categories of agents, namely anticoagulatory agents and antiplatelet agents.

Antivitamin K compounds constitute a very important family among the anticoagulatory agents. Given that these compounds are active via the oral route, they are used in numerous indications. However, their use is still limited by certain disadvantages and in particular the risks of haemorrhages caused by them and the difficulty of adapting the dosage to a long-term treatment.

Heparins constitute the second category of anticoagulatory agents. They are extractive biological substances of the glycosaminoglycan family, which are oligosaccharide compounds with varying chain lengths and degrees of sulphation. Heparins are used in various types of thromboses, in particular in the treatment or prevention of venous thromboses, optionally combined with other therapies.

The disadvantage of heparins lies in their high anticoagulatory activity which may cause haemorrhages, and in their sensitivity to certain serum factors such as pf4, which requires the use of relatively high doses.

Moreover, heparins are very heterogeneous products. It is therefore difficult to evaluate their mode of action, to assess the contribution of each of the components in the overall activity of heparin, and, consequently, to increase the antithrombotic activity without increasing the side effects.

A first solution to the abovementioned disadvantages has been provided by low-molecular weight heparins. These heparins are obtained by fragmentation (depolymerisation) of oligosaccharide chains using chemical or enzymatic agents. In particular, depolymerisation has been described by a treatment of a heparin ester in the presence of a strong base (EP 40144). It may also be carried out by treating heparin in the presence of nitrous acid, or by the action of a heparinase (EP 64452). These various methods lead to mixtures of oligosaccharides having the general structure of the polysaccharides which make up heparin, but having a mean molecular weight which is smaller by weight. More particularly, the investigations were directed mainly towards heparin-derived mixtures having very short oligosaccharide chains. Thus, Patent EP 27089 indicates that heparin-derived oligosaccharide mixtures containing not more than 8 saccharide units possess an antithrombotic specific activity which is greater than heparin. Similarly, hexasaccharides have been prepared and their antithrombotic properties studied (EP 64452). More recent Patents, EP 84 999 and EP 301 618, on heparin-derived polysaccharides such as hexa-, penta- and tetrasaccharides, may also be mentioned.

However, the products described so far have not enabled the problems encountered with heparins to be resolved in a completely satisfactory manner. In particular, it has not been possible to confirm in vivo the correlation between the mean molecular mass of the products and their side effects.

The applicant has now shown that it is possible to obtain, from native or depolymerised heparins, oligosaccharide mixtures having greatly improved antithrombin properties, and therefore better therapeutic potential.

In effect, the applicant has shown, unexpectedly, that a substantial part of the antithrombotic activity of heparin was present in a small and homogeneous fraction.

The present invention results more particularly from the identification of monodisperse fractions of heparin having a mean molecular mass of about 6 kD and possessing a high antithrombin activity.

As illustrated in the examples, it is therefore possible to obtain mixtures possessing a particularly high antithrombotic activity by calibrating the molecular mass and by reducing the polydispersity.

One subject of the invention is a mixture of sulphated oligosaccharides having the general structure of the constituent oligosaccharides of heparin, characterised in that it has a mean molecular mass by weight of 6±0.6 kD and a polydispersity of about 1, and in that it possesses the capacity to inhibit the generation of thrombin.

The polydispersity corresponds to the ratio of the mean molecular mass of the mixture to its mean molecular weight expressed in numerical terms. It provides information on the molecular homogeneity of the mixture. The closer this value is to 1, the more homogeneous is the mixture.

In addition to their antithrombin properties, the mixtures of the invention possess particularly advantageous pharmacokinetic properties.

Consequently, compared with native heparin and its depolymerised forms, the mixtures of the invention exhibit a lower sensitivity to serum factors such as pf4, which increases their therapeutic potential.

Other advantages of the mixtures of the invention lie in particular in the reduction of certain undesirable side effects such as:

thrombocytopenic effect. One of the disadvantages of the known mixtures derived from heparin stems from the drop in the number of platelets which they can bring about. This undesirable effect is substantially reduced when the mixtures of the invention are used, immunogenic reactions. When such reactions are too intense, it is evident that the therapeutic efficacy of the products is reduced. The weak immunogenicity of the mixtures of the invention constitutes another of their very advantageous pharmacological characteristics.

Furthermore, other advantages of the mixtures of the invention lie in particular in their excellent plasmatic bioavailability and half-life.

The properties described above permit a particularly effective pharmacological use especially in the prophylaxis and treatment of venous or arterial thromboses. Moreover, they should permit the use of higher doses in vivo without increasing the risks of haemorrhage.

In a preferred mode, the mixtures of the invention are more particularly depolymerised heparin fractions.

As indicated above, the depolymerised heparin may be obtained by any chemical, enzymatic or other technique known to a person skilled in the art, which enable the oligosaccharide chains of heparin to be fragmented. In particular, the methods described in Patents EP 40144, EP 64452, EP 37319 or EP 337327 are suitable for the invention.

Even more preferably, the mixtures of the invention consist of oligosaccharides having a 2-O-sulpho-4-enopyranosuronic acid at one of their ends.

A particularly advantageous mixture consists of a fraction of heparin which is depolymerised by the action of a base on a heparin ester.

The antithrombin activity of the mixtures of the invention may be demonstrated in a test in which the generation of thrombin is initiated in the presence of human thromboplastin (extrinsic route) or by contact (intrinsic route). Such a test has been described previously (Hemker et al., Thromb. Haemostas. 56, 9–17, 1986).

This activity may be expressed quantitatively by the amount of product required for 25% inhibition of the generation of thrombin. Thus, the increase in activity of the mixtures of the invention is clearly evident since their antithrombin specific activity in vitro is surprisingly increased by a factor above 100% compared with the heparin used at the beginning. Taking into account the particularly advantageous pharmacokinetic properties of the mixtures of the invention, this increase in specific activity is even greater in vivo.

More particularly, the mixtures of the invention permit, in a test carried out on plasma low in platelets, 25% inhibition of the generation of thrombin at concentrations below 300 ng/ml.

Another subject of the invention relates to a method of preparing a mixture as defined above, characterised in that a heparin or a depolymerised heparin is fractionated by gel filtration.

The process of the invention brings into play several parameters whose control makes it possible to calibrate the molecular mass of the final mixture and to determine its polydispersity. These parameters are in particular the ionic strength of the eluant and the nature of the support used.

More preferably, the fractionation is characterised in that the stages consisting in (i) dissolving the starting heparin or depolymerised heparin in the eluant, (ii) passing the solution thus obtained through a column at least containing the solid support for the gel filtration equilibrated beforehand with the same eluant, and (iii) recovering the fractions of the desired molecular weight, are carried out successively.

In a specific embodiment of the invention, the use of a depolymerised heparin as starting heparin is preferred.

Even more preferably, a heparin depolymerised by the action of a base on a heparin ester is used. In particular, the depolymerisation may be carried out in an aqueous medium or in an inert organic solvent under the action of an organic or inorganic base such as for example sodium or potassium hydroxide, an alkali metal carbonate or a tertiary amine (triethylamine, triethylenediamine and the like). The action of the base on the ester makes it possible to carry out a partial and controlled depolymerisation of the heparin without modifying its general structure.

More generally, the depolymerisation conditions described in Patent EP 40144 may be used in the present invention.

Various types of saline solutions such as solutions of sodium chloride may be mentioned as eluant which may be used in the method of the invention. However, the applicant has shown that in order to obtain fractions with the best qualities, it is particularly advantageous to carry out the fractionation using an eluant chosen from phosphate buffers such as in particular potassium phosphate, sodium phosphate or $NH_4H_2PO_4$. It is also possible to use $NaClO_4$ or $NH_4NO_3$ solutions which make it possible to obtain mixtures with excellent characteristics.

The concentration of the eluant, and therefore its ionic strength, are adjusted to the final mixture desired. In particular, the concentration of the eluant is advantageously less than 1M and, even more preferably, between 0.1 and 0.5M.

When a phosphate buffer is used, it is particularly advantageous to carry out the procedure at concentrations of about 0.2M.

In the second stage of the method of the invention, the support used is generally chosen as a function of the mean molecular mass of the starting mixture (native or depolymerised heparin and the like), of the final product desired and of the behaviour of the starting mixture in the eluant used. Advantageously, a polyacrylamide-agarose type gel is used as support. The gels AcA 54, AcA 202, sephadex G-25 or G-50 or alternatively Biogel P30, which give excellent results, may be mentioned by way of example.

In a first particularly advantageous embodiment of the method of the invention, the solid support is divided among several columns arranged in series, during the second stage of the fractionation. This variant of the invention makes it possible to use substantial final amounts of gel filtration support without the disadvantages of the prior art, namely the phenomena of settling essentially. Thus, the separation is substantially more distinct, including in the high molecular weight range, in a single fractionation operation, and the supports are more easily regenerated.

The number of columns used is adjusted by a person skilled in the art as a function of the volume and the nature of the gel used so as to obtain the best balance between efficiency of the separation and the adverse effect due to the settling of the gel.

For practical considerations relating to the implementation, the preferred number of columns generally used in the second stage of the process is less than 20.

By way of illustration, 40 litres of AcA 202 gel may be divided into 10 4-litre columns.

In another particularly advantageous embodiment of the method of the invention, at least 2 types of supports having differing separation characteristics are used successively in the second stage of the fractionation. This variant of the invention makes it possible to obtain a final fractionation of better quality.

By way of example, the fractionation may be carried out on the following sequence of gels: AcA 202 - AcA 54 - AcA 202.

For a better implementation of the invention, it is important to use high amounts of gel so as to achieve a more distinct separation and to obtain greater homogeneity. However, given the fairly slow flow rates used for this type of gel filtration, the gel volume should be adapted to the amount of product to be separated so as to obtain the best equilibrium between the separation and the effect of longitudinal diffusion.

Advantageously, in the method of the invention, the starting heparin (g)/gel volume (1) ratio is less than 2, and even more preferably between 0.5 and 1.5.

The invention also relates to a method of preparation of weakly dispersed mixtures of oligosaccharides with a molecular weight which is calibrated by fractionation of heparin or depolymerised heparin by gel filtration on a solid support, characterised in that the solid support is divided among several columns arranged in series.

Another subject of the invention relates to a pharmaceutical composition having a mixture as defined above as active ingredient. Such a composition may be used in a particularly advantageous manner in the prophylaxis or treatment or prevention of thrombotic accidents. More specifically, it may be used:

in the prevention of venous thromboses in situations where a risk exists, in the prevention of arterial thrombotic accidents, especially in the case of myocardial infarction, in post-operative regime, in the prevention of venous thromboses in surgical patients, or alternatively, in the prevention of thromboses in surgical material.

The present invention will be more completely described with the aid of the following examples which should be considered as illustrative and nonlimiting.

EXAMPLE 1

Preparation of Mixtures According to the Invention

Depolymerisation of heparin

A solution of 25 g of benzethonium chloride in 125 ml of water is added to a solution of 10 g of sodium heparinate in 100 ml of water. The product obtained at room temperature is filtered, washed with water and then dried. 15 g of the benzethonium heparinate thus obtained are dissolved in 75 ml of methylene chloride to which 15 ml of benzyl chloride are added. The solution is heated at a temperature of between 25 and 35° C. for 25 hours. 90 ml of a 10% solution of sodium acetate in methanol are then added, filtered, washed with methanol and dried. 10 g of the heparin benzyl ester obtained in the form of a sodium salt under the conditions described above are dissolved in 250 ml of water. 0.9 g of sodium hydroxide is added to this solution heated to about 60° C. The temperature is maintained for 1 hour 30 minutes at about 60° C. and the reaction mixture is then cooled to around 20° C. and neutralised by adding dilute hydrochloric acid. The mixture is then adjusted to a sodium chloride concentration of 10% and the product is precipitated in 750 ml of methanol, filtered and dried.

Several glass columns are used for the fractionation:

(a) 1 column with a diameter of 95 mm and a height of 2 m containing 14 litres of the AcA 202 gel (gel in the form of polyacrylamide-agarose beads, with a diameter of between 60 and 140 µm), (b) 1 column with a diameter of 50 mm and a height of 2 m containing 4 litres of the AcA 54 gel (gel in the form of polyacrylamide-agarose beads, with a diameter of between 60 and 140 µm), (c) 2 columns with a diameter of 50 mm and a height of 1 m containing 2 litres of the AcA 202 gel.

A solution containing 20 g of heparin depolymerised under the conditions described above is placed at the top of the column (a) and eluted using a mobile phase consisting of a 0.33M solution of NaCl at a flow rate of 210 ml/hour.

The fractions are collected at the outlet of the column (a) and loaded onto the top of the column (b). The elution is carried out with the same solution and the fractions collected are passed successively through the 2 columns (c).

This treatment enables a fraction having the following characteristics to be separated efficiently and recovered at the outlet of the column (c):

Molecular weight: 6100+/−200

Polydispersity: 1.01

EXAMPLE 2

10 columns with an internal diameter of 2.5 cm and a height of 50 cm, each containing about 0.25 litre of the AcA 202 gel, are connected in series, a solution containing 2 g of heparin, which is depolymerised under the conditions of Example 1, is loaded onto the top of the device and eluted using a 0.2M aqueous solution of $KH_2PO_4$ at a flow rate of 0.42 ml/min, 113 fractions of 12.6 ml are collected starting from 21 hours.

The characteristics of these fractions are given in Table 1, in which the mean molecular mass was determined by refractometry.

EXAMPLE 3

The procedure is as in Example 2:

10 columns with an internal diameter of 10 cm and a height of 50 cm, each containing 3 to 4 litres of the AcA 202 gel, are connected in series, a solution containing 30 g of heparin, which is depolymerised under the conditions of Example 1, is loaded onto the top of the device and eluted using a 0.2M aqueous solution of $KH_2PO_4$ at a flow rate of 6.8 ml/min.

Fractions having the desired polydispersity characteristics are obtained.

EXAMPLE 4

The antithrombin activity of the mixtures of the invention is measured on plasma stimulated by human thromboplastin (extrinsic route) or by contact (phospholipids+kaolin: intrinsic route) under the conditions described above (cf Hemker et al., mentioned above). The activity is estimated by the decrease in the peak of the thrombin generation curve relative to a control carried out in the presence of buffer alone. The results are expressed as the IC25: concentration required to obtain 25% inhibition of the generation of thrombin.

Procedure:

¼ volume of 50 mM tris-HCl buffer, 0.1M NaCl, pH 7.35 with 0.5 mg/ml bovine albumin, containing various concentrations of test samples, is added to one volume of plasma. After incubating for 5 min at 37° C., the generation of thrombin is initiated by the addition of ¼ volume of thromboplastin 1:40 diluted in 0.1M $CaCl_2$ (extrinsic system) or by 6 µM of phospholipids (20% phosphatidylserine, 80% phosphatidylcholine) and 0.15 mg/ml of kaolin in 0.1M $CaCl_2$ (intrinsic system). The generation of thrombin is obtained by measuring, at regular intervals (15–30 sec), the amydolytic activity on the substrate S2238, a 405 nM chromogenic substrate specific for thrombin. Various concentrations of the samples are tested in order to obtain 25% inhibition of the control.

Results:

On plasma low in platelets 1) extrinsic route

Depolymerised starting heparin: IC25=450 ng/ml

Mixture prepared in Example 1: IC25=200 ng/ml

Activity gain: 125%

2) intrinsic route

Depolymerised starting heparin: IC25=550 ng/ml

Mixture prepared in Example 1: IC25=250 ng/ml

Activity gain: 120%

On plasma high in platelets

Depolymerised starting heparin: IC25=1100 ng/ml

Mixture prepared in Example 1: IC25=500 ng/ml

Under the same conditions, native heparin (nondepolymerised, nonfractionated) possesses no inhibitory activity at 2500 ng/ml.

TABLE 1

| FRACTION NO. | MEAN MOLECULAR MASS | POLYDISPERSITY |
|---|---|---|
| 14–17 | 10712 | 1.027 |
| 18–20 | 8400 | 1.013 |

TABLE 1-continued

| FRACTION NO. | MEAN MOLECULAR MASS | POLYDISPERSITY |
| --- | --- | --- |
| 21–22 | 7519 | 1.010 |
| 23–24 | 6986 | 1.011 |
| 26–27 | 6365 | 1.008 |
| 28–31 | 5874 | 1.009 |
| 32–35 | 5295 | 1.011 |
| 36–40 | 4761 | 1.012 |
| 42–46 | 4192 | 1.013 |
| 48–53 | 3608 | 1.016 |
| 56–61 | 2988 | 1.019 |
| 64–70 | 2359 | 1.023 |
| 75–80 | 1758 | 1.029 |
| 83–85 | 1476 | 1.028 |
| 88–94 | 1176 | 1.027 |

We claim:

1. A mixture of sulfated oligosaccharides having the structure of constituent oligosaccharides of heparin, that has a mean molecular mass of 6±0.6 kD and a polydispersity of 1 to 1.029, and that possesses a capacity to inhibit the generation of thrombin.

2. The mixture according to claim 1, wherein the heparin is a depolymerized heparin fraction.

3. The mixture according to claim 2, consisting of constituent oligosaccharides having a 2-O-sulpho-4-enopyranosuronic acid at one of their ends.

4. The mixture according to claim 3, wherein the heparin is a depolymerized heparin that is depolymerized by the action of a base on an ester of the heparin.

5. The mixture according to claim 1, having the capacity, in a test on plasma low in platelets stimulated by human thromboplastin or by contact, to inhibit the generation of thrombin by 25% at concentrations less than 400 ng/ml.

6. A composition comprising the mixture of oligosaccharides according to claim 1 and a buffer.

7. A method of treating or preventing venous or arterial thromboses comprising administering the mixture according to claim 1 to a patient.

8. A method according to claim 7 wherein the arterial thromboses is an arterial thrombotic accident.

9. The method according to claim 8 wherein the arterial thrombotic accident is myocardial infarction.

10. The method according to claim 7 wherein the preventing of the venous thromboses is in a post-operative regime on a surgical patient.

11. A method of inhibiting the generation of thrombin comprising administering the mixture of oligosaccharides according to claim 1 to a patient.

12. A method of preventing thromboses in a surgical material comprising contacting the material with the mixture of claim 1.

* * * * *